US010314894B2

United States Patent
Wu et al.

(10) Patent No.: US 10,314,894 B2
(45) Date of Patent: Jun. 11, 2019

(54) TREATMENT OF CARDIO-RENAL DISEASE USING PCSK6

(71) Applicant: THE CLEVELAND CLINIC FOUNDATION, Cleveland, OH (US)

(72) Inventors: Qingyu Wu, Orange Village, OH (US); Shenghan Chen, Beachwood, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 0 days.

(21) Appl. No.: 14/620,278

(22) Filed: Feb. 12, 2015

(65) Prior Publication Data

US 2016/0058848 A1  Mar. 3, 2016

Related U.S. Application Data

(60) Provisional application No. 61/939,016, filed on Feb. 12, 2014.

(51) Int. Cl.
  *A61K 38/48* (2006.01)
(52) U.S. Cl.
  CPC .......... *A61K 38/482* (2013.01); *C12Y 304/21* (2013.01)
(58) Field of Classification Search
  CPC ........................... A61K 38/482; C12Y 304/21
  See application file for complete search history.

(56) References Cited

U.S. PATENT DOCUMENTS

| 7,176,013 | B2* | 2/2007 | Wu | C12N 9/6424 424/94.64 |
|---|---|---|---|---|
| 2005/0026255 | A1 | 2/2005 | Morser et al. | |
| 2011/0160128 | A1* | 6/2011 | Jiang et al. | A61K 38/482 514/4.8 |
| 2011/0306069 | A1* | 12/2011 | Chen et al. | G01N 33/6893 435/7.92 |

OTHER PUBLICATIONS

Scerri et al. "PCSK6 is associated with handedness in individuals with dyslexia" Human Molecular Genetics, 2011, vol. 20, No. 3.*
Bak et al. "Physiochemical and Formulation Developability Assessment for Therapeutic Peptide Delivery—A Primer" AAPS J., 17(1):144-55 (2015).*
Dong et al. "Plasma Soluble Corin in Patients With Heart Failure" Circ heart Fail Mar. 2010 pp. 207-211.*
Polzin et al. "Decreased renal corin expression contributes to sodium retention in proteinuric kidney diseases" Kidney International ( 2010) 78, 650-659.*
Beaubien, Guy, et al. "The distinct gene expression of the pro-hormone convertases in the rat heart suggests potential substrates." Cell and tissue research 279.3 (1995): 539-549.
Cui, Yujie, et al. "Role of corin in trophoblast invasion and uterine spiral artery remodelling in pregnancy." Nature 484.7393 (2012): 246-250.
Dong, Ningzheng, et al. "Corin mutation R539C from hypertensive patients impairs zymogen activation and generates an inactive alternative ectodomain fragment." Journal of Biological Chemistry 288.11 (2013): 7867-7874.
Dong, Ningzheng, et al. "Corin Mutations K317E and S472G from Preeclamptic Patients Alert Zymogen Activation and Cell Surface Targeting." Journal of Biological Chemistry 289.25 (2014): 17909-17916.
Dries, Daniel L., et al. "Corin gene minor allele defined by 2 missense mutations is common in blacks and associated with high blood pressure and hypertension." Circulation 112.16 (2005): 2403-2410.
Dries, Daniel L. "Process Matters Emerging Concepts Underlying Impaired Natriuretic Peptide System Function in Heart Failure." Circulation: Heart Failure 4.2 (2011): 107-110.
Gladysheva, Irina P., et al. "Corin overexpression improves cardiac function, heart failure, and survival in mice with dilated cardiomyopathy." Hypertension 61.2 (2013): 327-332.
Li, Jian-Ping, et al. "The association between paired basic amino acid cleaving enzyme 4 gene haplotype and diastolic blood pressure." Chinese medical journal 117.3 (2004): 382-388.
Rockwell, Nathan C., et al. "Precursor processing by kex2/furin proteases." Chemical reviews 102.12 (2002): 4525-4548.
Rame, J. Eduardo, et al. "Corin I555 (P568) allele is associated with enhanced cardiac hypertrophic response to increased systemic afterload." Hypertension 49.4 (2007): 857-864.
Seidah, Nabil G., et al. "The multifaceted proprotein convertases: their unique, redundant, complementary, and opposite functions." Journal of Biological Chemistry 288.30 (2013): 21473-21481.
Seidah, Nabil G., et al. "PCSK9 A Key Modulator of Cardiovascular Health." Circulation research 114.6 (2014): 1022-1036.
Wang, Wei, et al. "Corin variant associated with hypertension and cardiac hypertrophy exhibits impaired zymogen activation and natriuretic peptide processing activity." Circulation research 103.5 (2008): 502-508.
Yan, Wei, et al. "Corin, a transmembrane cardiac serine protease, acts as a pro-atrial natriuretic peptide-converting enzyme." Proceedings of the National Academy of Sciences 97.15 (2000): 8525-8529.
Yan, Wei, et al. "Corin, a mosaic transmembrane serine protease encoded by a novel cDNA from human heart." Journal of Biological Chemistry 274.21 (1999): 14926-14935.

* cited by examiner

*Primary Examiner* — Louise W Humphrey
*Assistant Examiner* — Stephen A Perkins
(74) *Attorney, Agent, or Firm* — Tarolli, Sundheim, Covell & Tummino LLP

(57) ABSTRACT

A method of treating a cardio-renal disease is described that includes administering to a subject in need thereof a therapeutically effective amount of proprotein convertase subtilisin/kexin-6 (PCSK6), or an effective fragment thereof, which functions as a corin activator.

14 Claims, 6 Drawing Sheets
Specification includes a Sequence Listing.

Fig. 1a

"MPPRAPPAPGPRPPPRAAAATDTAAGAGGAGGAGGAGGPGFRPL

APRPWRWLLLLALPAACSAPPPRPVYTNHWAVQVLGGPAEADRVAAAHGYLNLGQIGN

LEDYYHFYHSKTFKRSTLSSRGPHTFLRMDPQVKWLQQQEVKRRVKRQVRSDPQALYF

NDPIWSNMWYLHCGDKNSRCRSEMNVQAAWKRGYTGKNVVVTILDDGIERNHPDLAPN

YDSYASYDVNGNDYDPSPRYDASNENKHGTRCAGEVAASANNSYCIVGIAYNAKIGGI

RMLDGDVTDVVEAKSLGIRPNYIDIYSASWGPDDDGKTVDGPGRLAKQAFEYGIKKGR

QGLGSIFVWASGNGGREGDYCSCDGYTNSIYTISVSSATENGYKPWYLEECASTLATT

YSSGAFYERKIVTTDLRQRCTDGHTGTSVSAPMVAGIIALALEANSQLTWRDVQHLLV

KTSRPAHLKASDWKVNGAGHKVSHFYGFGLVDAEALVVEAKKWTAVPSQHMCVAASDK

RPRSIPLVQVLRTTALTSACAEHSDQRVVYLEHVVVRTSISHPRRGDLQIYLVSPSGT

KSQLLAKRLLDLSNEGFTNWEFMTVHCWGEKAEGQWTLEIQDLPSQVRNPEKQGKLKE

WSLILYGTAEHPYHTFSAHQSRSRMLELSAPELEPPKAALSPSQVEVPEDEEDYTAQS

TPGSANILQTSVCHPECGDKGCDGPNADQCLNCVHFSLGSVKTSRKCVSVCPLGYFGD

TAARRCRRCHKGCETCSSRAATQCLSCRRGFYHHQEMNTCVTLCPAGFYADESQKNCL

KCHPSCKKCVDEPEKCTVCKEGFSLARGSCIPDCEPGTYFDSELIRCGECHHTCGTCV

GPGREECIHCAKNFHFHDWKCVPACGEGFYPEEMPGLPHKVCRRCDENCLSCAGSSRN

CSRCKTGFTQLGTSCITNHTCSNADETFCEMVKSNRLCERKLFIQFCCRTCLLAG"

Fig. 1b

```
  1 tcgcgggccg aggacgcctc tggggcggca ccgcgtcccg agagcccag aagtcggcgg
 61 ggaagttccc ccggtggggg gcgtttcggg cctccggac ggctctcggc cccggagccc
121 ggtcgcagga gcgcgggccc ggggcggga cgcgccgcg gcgcctcct cctccccggc
181 tcccgcccgc ggcggtgttg gcggcggcgg tggcggcggc ggcggcgctt ccccggcgcg
241 gagcggcttt aaaaggcggc actccacccc ccggcgcact cgcagctcgg gcgccgcgcg
301 agcctgtcgc cgctatgcct ccgcgcgcgc cgcctgcgcc cgggcccgg ccgccgcccc
361 gggccgccgc cgccaccgac accgccgcgg gcgcggggg cgcggggggc gcggggggcg
421 ccggcgggcc cgggttccgg ccgctcgcgc cgcgtccctg gcgctggctg ctgctgctgg
481 cgctgcctgc cgcctgctcc gcgccccgc cgcgccccgt ctacaccaac cactgggcgg
541 tgcaagtgct gggcggcccg gccgaggcgg accgcgtggc ggcggcgcac gggtacctca
601 acttgggcca gattggaaac ctggaagatt actaccattt ttatcacagc aaaaccttta
661 aaagatcaac cttgagtagc agaggccctc acaccttcct cagaatggac ccccaggtga
721 aatggctcca gcaacaggaa gtgaaacgaa gggtgaagag acaggtgcga agtgacccgc
781 aggccctta cttcaacgac ccatttggt ccaacatgtg gtacctgcat tgtggcgaca
841 agaacagtcg ctgccggtcg gaaatgaatg tccaggcagc gtgaagagg ggctacacag
901 gaaaaaacgt ggtggtcacc atccttgatg atggcataga gagaaatcac cctgacctgg
```

Fig. 1b (Cont.)

```
 961 ccccaaatta tgattcctac gccagctacg acgtgaacgg caatgattat gacccatctc
1021 cacgatatga tgccagcaat gaaaataaac acggcactcg ttgtgcggga gaagttgctg
1081 cttcagcaaa caattcctac tgcatcgtgg gcatagcgta caatgccaaa ataggaggca
1141 tccgcatgct ggacggcgat gtcacagatg tggtcgaggc aaagtcgctg ggcatcagac
1201 ccaactacat cgacatttac agtgccagct gggggccgga cgacgacggc aagacggtgg
1261 acgggcccgg ccgactggct aagcaggctt tcgagtatgg cattaaaaag ggccggcagg
1321 gcctgggctc catttcgtc tgggcatctg ggaatggcgg gagagagggg gactactgct
1381 cgtgcgatgg ctacaccaac agcatctaca ccatctccgt cagcagcgcc accgagaatg
1441 gctacaagcc ctggtacctg gaagagtgtg cctccaccct ggccaccacc tacagcagtg
1501 gggccttta tgagcgaaaa atcgtcacca cggatctgcg tcagcgctgt accgatggcc
1561 acactgggac ctcagtctct gccccatgg tggcgggcat catcgccttg gctctagaag
1621 caaacagcca gttaacctgg agggacgtcc agcacctgct agtgaagaca tcccggccgg
1681 cccacctgaa agcgagcgac tggaaagtga acggcgcggg tcataaagtt agccatttct
1741 atggatttgg tttggtggac gcagaagctc tcgttgtgga ggcaaagaag tggacagcag
1801 tgccatcgca gcacatgtgt gtggccgcct cggacaagag acccaggagc atcccttag
1861 tgcaggtgct gcggactacg gcctgacca gcgcctgcgc ggagcactcg gaccagcggg
1921 tggtctactt ggagcacgtg gtggttcgca cctccatctc acacccacgc cgaggagacc
1981 tccagatcta cctggtttct ccctcgggaa ccaagtctca acttctggca agaggttgc
2041 tggatctttc caatgaaggg tttacaaact gggaattcat gactgtccac tgctggggag
2101 aaaaggctga agggcagtgg accttggaaa tccaagatct gccatcccag gtccgcaacc
2161 cggagaagca agggaagttg aaagaatgga gcctcatact gtatggcaca gcagagcacc
2221 cgtaccacac cttcagtgcc catcagtccc gctcgcggat gctggagctc tcagcccag
2281 agctggagcc acccaaggct gcctgtcac cctcccaggt ggaagttcct gaagatgagg
2341 aagattacac agctcaatcc accccaggct ctgctaatat tttacagacc agtgtgtgcc
2401 atccggagtg tggtgacaaa ggctgtgatg gccccaatgc agaccagtgc ttgaactgcg
2461 tccacttcag cctggggagt gtcaagacca gcaggaagtg cgtgagtgtg tgccccttgg
2521 gctactttgg ggacacagca gcaagacgct gtcgccggtg ccacaagggg tgtgagacct
2581 gctccagcag agctgcgacg cagtgccgtc cttgccgccg cgggttctat caccaccagg
2641 agatgaacac ctgtgtgacc ctctgtcctg caggatttta tgctgatgaa agtcagaaaa
2701 attgccttaa atgccaccca agctgtaaaa agtgcgtgga tgaacctgag aaatgtactg
2761 tctgtaaaga aggattcagc cttgcacggg gcagctgcat tcctgactgt gagccaggca
2821 cctactttga ctcagagctg atcagatgtg gggaatgcca tcacacctgc ggaacctgcg
2881 tggggccagg cagagaagag tgcattcact gtgcgaaaaa cttccacttc cacgactgga
2941 agtgtgtgcc agcctgtggt gagggcttct acccagaaga gatgccgggc ttgccccaca
3001 aagtgtgtcg aaggtgtgac gagaactgct tgagctgtgc aggctccagc aggaactgta
3061 gcaggtgtaa gacgggcttc acacagctgg ggacctcctg catcaccaac cacacgtgca
3121 gcaacgctga cgagacattc tgcgagatgg tgaagtccaa ccggctgtgc gaacggaagc
3181 tcttcattca gttctgctgc cgcacgtgcc tcctggccgg gtaagggtgc ctagctgccc
3241 acagagggca ggcactccca tccatccatc cgtccacctt cctccagact gtcggccaga
3301 gtctgtttca ggagcggcgc cctgcacctg acagctttat ctccccagga gcagcatctc
3361 tgagcaccca agccaggtgg gtggtggctc ttaaggaggt gttcctaaaa tggtgatatc
3421 ctctcaaatg ctgcttgttg gctccagtct tccgacaaac taacaggaac aaaatgaatt
3481 ctgggaatcc acagctctgg ctttggagca gcttctggga ccataagttt actgaatctt
3541 caagaccaaa gcagaaaaga aaggcgcttg gcatcacaca tcactcttct ccccgtgctt
3601 ttctgcggct gtgtagtaaa tctccccggc ccagctggcg aaccctgggc catcctcaca
3661 tgtgacaaag ggccagcagt ctacctgctc gttgcctgcc actgagcagt ctgggacgg
3721 tttggtcaga ctataaataa gataggtttg agggcataaa atgtatgacc actggggccg
3781 gagtatctat ttctacatag tcagctactt ctgaaactgc agcagtggct tagaaagtcc
3841 aattccaaag ccagaccaga agattctatc cccgcagcg ctctcctttg agcaagccga
3901 gctctccttg ttaccgtgtt ctgtctgtgt cttcaggagt ctcatggcct gaacgaccac
3961 ctcgacctga tgcagagcct tctgaggaga ggcaacagga ggcattctgt ggccagccaa
4021 aaggtacccc gatggccaag caattcctct gaacaaaatg taaagccagc catgcattgt
4081 taatcatcca tcacttccca ttttatggaa ttgcttttaa aatacatttg gcctctgccc
4141 ttcagaagac tcgtttttaa ggtggaaact cctgtgtctg tgtatattac aagcctacat
4201 gacacagttg gatttattct gccaaacctg tgtaggcatt ttataagcta catgttctaa
4261 tttttaccga tgttaattat tttgacaaat atttcatata ttttcattga aatgcacaga
4321 tctgcttgat caattccctt gaataggaa gtaacatttg ccttaaattt tttcgacctc
4381 gtctttctcc atattgtcct gctccctgt ttgacgacag tgcatttgcc ttgtcacctg
4441 tgagctggag agaacccaga tgttgtttat tgaatctaca actctgaaag agaaatcaat
```

Fig. 1b (Cont.)

```
4501 gaagcaagta caatgttaac cctaaattaa taaaagagtt aacatcccat ggcaaaaaaa
4561 aaaaaaaaaa a//
```

US 10,314,894 B2

TREATMENT OF CARDIO-RENAL DISEASE USING PCSK6

CROSS-REFERENCE TO RELATED APPLICATIONS

This Application claims priority to U.S. Provisional Patent Application Ser. No. 61/939,016, filed Feb. 12, 2014, which is incorporated herein by reference.

STATEMENT ON FEDERALLY FUNDED RESEARCH

The present invention was supported, at least in part, by government support by the Nation Institutes of Health under Grant Nos. R01HL089298 and R01HD064634. The Government has certain rights in this invention.

SEQUENCE LISTING

The instant application contains a Sequence Listing which has been submitted in ASCII format via EFS-Web and is hereby incorporated by reference in its entirety. Said ASCII copy, created on Feb. 10, 2015, is named PCSK6 for treatment of cardio-renal disease (CCF-023177 US ORD)_ST25, and is 27,873 bytes in size.

BACKGROUND

Hypertension is a common cardiovascular disease. In the United States, more than 30% of adults develop hypertension. The disease is a well-known risk factor for major cardiovascular diseases such as myocardial infarction, heart failure, renal failure, and stroke. In most patients with hypertension, the underlying cause remains unknown, indicating that additional contributing factors remain to be discovered. To date, genetic mutations that impair sodium homeostasis have been reported in some hypertensive patients. These findings are consistent with the notion that hypertension reflects inadequate control of salt and body fluid balance.

Atrial natriuretic peptide (ANP) is a key hormone for sodium homeostasis and normal blood pressure. Mutations that alter ANP amino acids have been found in hypertensive patients. In heart cells, ANP is produced as a precursor, pro-ANP, which is activated to ANP by corin, a membrane-bound serine protease. Yan et al., Proc Natl Acad Sci U.S.A 97, 8525-8529 (2000). This function of corin is important for maintaining normal blood pressure. As a trypsin-like enzyme, corin is made as an inactive zymogen, which is activated by proteolytic cleavage at a conserved site, Arg-801↓Ile-802 (FIG. 2a). Yan et al., J Biol Chem 274, 14926-14935 (1999). CORIN gene variants and mutations preventing corin activation have been identified in patients with hypertension and pre-eclampsia. This zymogen activation step is critical for corin activity. For many years, however, the enzyme responsible for corin activation remained unidentified.

SUMMARY OF THE INVENTION

The inventors show that proprotein convertase subtilisin/kexin-6 (PCSK6) is a primary corin activator. In cultured cardiomyocytes and HEK293 cells, corin zymogen activation was inhibited in the presence of PCSK inhibitors and small interfering RNAs that specifically inhibit PCSK6 expression. In contrast, increased corin activation was found in cells overexpressing PCSK6. In assays with purified recombinant PCSK6, corin activation was shown to occur at the specific site. In addition, corin variants identified in hypertensive and preeclamptic patients were defective in PCSK6-dependent activation. The results indicate that PCSK6 is the elusive corin activator and that PCSK6 may be used as a therapeutic agent to enhance corin activity to treat patients with hypertension and heart disease.

BRIEF DESCRIPTION OF THE FIGURES

The present invention may be more readily understood by reference to the following drawings, wherein:

FIGS. 1a-1b provides the amino acid sequence for the human PCSK6 protein (SEQ ID NO: 1), and the nucleotide sequence for cDNA expressing PCSK6 (SEQ ID NO: 2).

DETAILED DESCRIPTION OF THE INVENTION

Figures 2A, 2B, 2C, 2D, 2E, 2F, 2G:
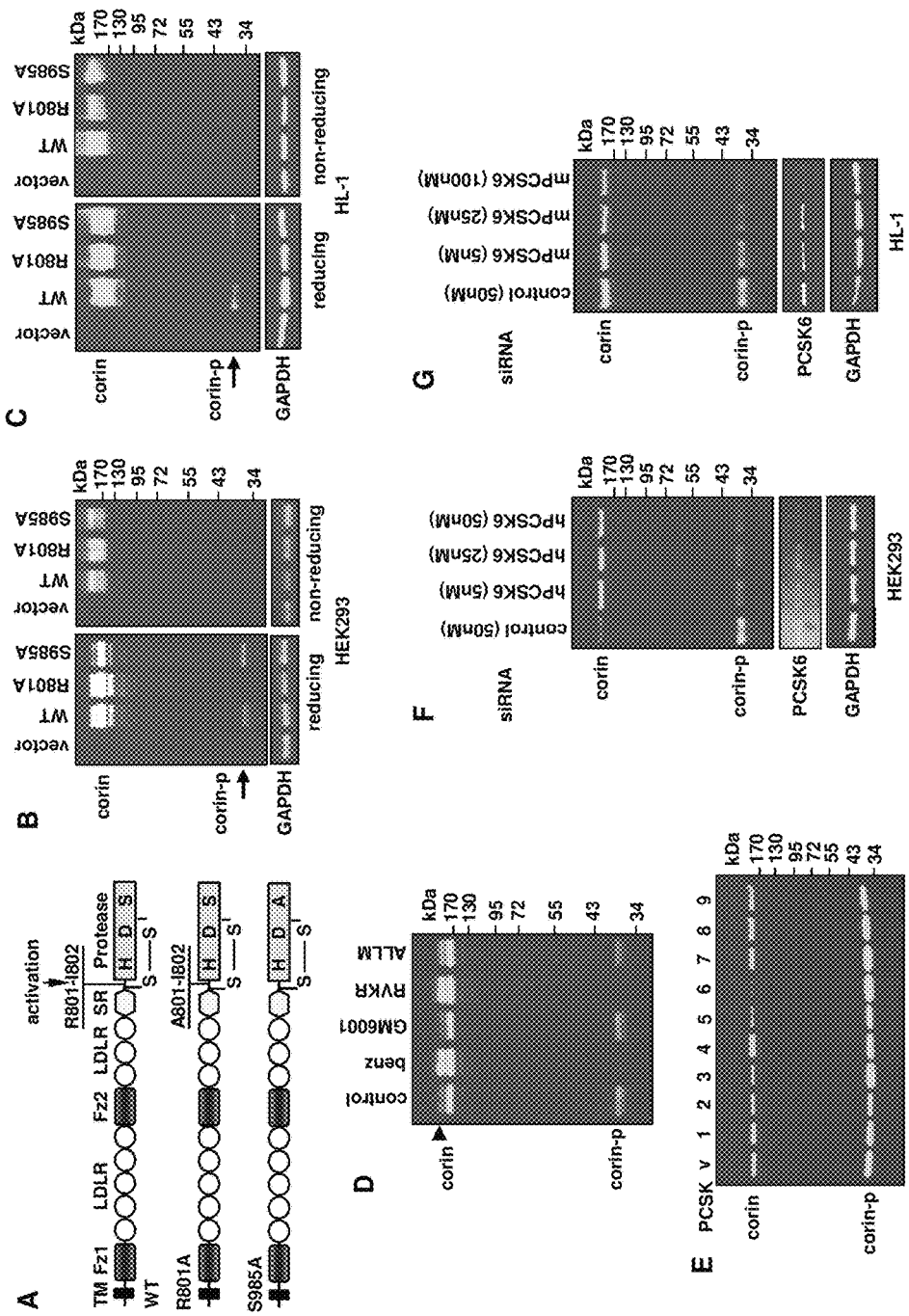
FIG. 2(a-g) provides graphs and images showing that corin activation cleavage in HEK293 and HL-1 cells. (a) Schematic illustration of corin domains and mutants. TM, transmembrane; Fz, frizzled; LDLR, LDL receptor; SR, scavenger receptor. Corin activation site at R801-I802 is indicated by an arrow. In mutant R801A, the activation cleavage site is mutated. In mutant S985A, the catalytic serine is mutated. A disulfide bond (s-s) connecting the propeptide and the protease domain is indicated. (b) and (c) Corin activation cleavage, as indicated by a 40-kDa band (corin-p), was detected in HEK293 cells and HL-1 cardiomyocytes by Western blotting under reducing conditions. As predicted by corin domain structure, the 40-kDa band was not detected when Western blotting was done under non-reducing conditions. (d) In HEK293 cells, corin activation cleavage was inhibited in the presence of benzamidine (banz) (serine protease inhibitor) and RVKR-cmk (RVKR) (PCSK protease inhibitor), but not GM6001 (metalloproteinase inhibitor) or ALLM (cysteine protease inhibitor). An arrowhead indicates corin zymogen on the cell surface. (e) Overexpression of PCSK6, but not other PCSKs, enhanced corin activation in HEK293 cells. In HEK293 (f) and HL-1 (g) cells, blocking PCSK6 expression by siRNAs targeting human (h) and mouse (m) PCSK6 genes inhibited corin activation.

The present invention provides methods of treating a cardio-renal disease that include administering to a subject in need thereof a therapeutically effective amount of proprotein convertase subtilisin/kexin-6 (PCSK6), or an effective fragment thereof, which functions as a corin activator.

Definitions

The terminology as set forth herein is for description of the embodiments only and should not be construed as limiting of the invention as a whole. As used in the description of the invention and the appended claims, the singular forms "a", "an", and "the" are inclusive of their plural forms, unless contraindicated by the context surrounding such.

"Treat", "treating", and "treatment", etc., as used herein, refer to any action providing a benefit to a subject at risk for or afflicted with a condition or disease such as heart failure, including improvement in the condition through lessening or suppression of at least one symptom, delay in progression of the disease, prevention or delay in the onset of the disease, etc. The subject may be at risk due to the presence of a risk factor such as high blood pressure, diabetes, being genetically predisposed to heart failure, and so on.

Within the present invention, a "therapeutically effective amount" of a composition is that amount which is sufficient to show a benefit (e.g., a reduction in a symptom associated with the disorder, disease, or condition being treated) while avoiding adverse side effects such as those typically associated with alternative therapies. The therapeutically effective amount may be administered in one or more doses.

As used herein, the term "pharmaceutically acceptable carrier" refers to carriers that do not negatively affect the biological activity of the therapeutic molecule or compound to be placed therein. The characteristics of the delivery vehicle will depend on the route of administration. Therapeutic compositions may contain, in addition to the active compound, diluents, fillers, salts, buffers, stabilizers, solubilizers, and other materials well known in the art. A pharmaceutically acceptable delivery vehicle can deliver the PCSK6 without unduly deleterious side effects in light of the severity of the disease and necessity of the treatment.

A subject, as defined herein, is an animal, preferably a mammal such as a domesticated farm animal (e.g., cow, horse, pig) or a pet (e.g., dog, cat). More preferably, the subject is a human. The subject may also be a subject in need of treatment of a cardio-renal disease. A subject in need of treatment of a cardio-renal disease can be a subject who has been diagnosed as having a disorder characterized by decreased corin activity. Such disorders include, but are not limited to heart failure and hypertension.

In one aspect, the invention provides a method of treating a cardio-renal disease. The method includes administering to a subject in need thereof a therapeutically effective amount of proprotein convertase subtilisin/kexin-6 (PCSK6) or an effective fragment thereof.

As used herein, proprotein convertase subtilisin/kexin-6 (PCSK6) refers to a protease found in mammals, and encoded by the PCSK6 gene in humans. PCSK6 belongs to the subtilisin-like proprotein convertase family. The members of this family are proprotein convertases that process latent precursor proteins into their biologically active products. PCSK6 is constitutively secreted into the extracellular matrix and expressed in many tissues, including neuroendocrine, liver, gut, and brain. PCSK6 is a calcium-dependent serine endoprotease that can cleave precursor protein at their paired basic amino acid processing sites. Some of its substrates are transforming growth factor beta related proteins, proalbumin, and von Willebrand factor. The amino acid sequence of PCSK6 is known in humans and the mouse; the sequences are assigned Reference Sequences numbers NP_001278238 and NP_001278113, respectively. See Wang et al., J Endocrinol., 222(1): 151-60 (2014), the disclosure of which is incorporated herein by reference.

As used herein, an "effective fragment" of PCSK6 is a portion of the PCSK6 polypeptide that retains the ability of PCSK6 to activate corin. In some embodiments, an effective fragment of PCSK6 is a soluble polypeptide comprising the serine endoprotease catalytic site. Effective fragments of PCSK6 include peptides comprising amino acid sequences sufficiently homologous to or derived from the amino acid sequence of PCSK6, e.g., the amino acid sequence shown in SEQ ID NO: 1, which include less amino acids than a full length PCSK6 protein and which retain the endoprotease activity of the PCSK6 protein. An effective fragment of a PCSK6 protein can be a polypeptide which is, e.g., 50, 100, 250, 500, or 750 or more amino acids in length.

The PCSK6 protein, polypeptide fragments thereof, mutants, truncations, derivatives, and splice variants of SEQ ID NO: 1 that display substantially equivalent or altered activity relative to SEQ ID NO: 1 are likewise contemplated. These variants may be deliberate, for example, such as modifications obtained through site-directed mutagenesis, or may be accidental, such as those obtained through mutations in hosts that are producers of the PCSK6 protein. Included within the scope of these terms are PCSK6 protein recited herein, as well as all substantially homologous analogs and allelic variants thereof.

Analogs may be made through substitution of conserved amino acids. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a PCSK6 protein is preferably replaced with another amino acid residue from the same side chain family. Alternatively, in another embodiment, mutations can be introduced randomly along all or part of the PCSK6 coding sequence, such as by saturation mutagenesis, and the resultant mutants can be screened for activity to identify mutants that retain activity. Following mutagenesis of SEQ ID NO: 2, the encoded protein can be expressed recombinantly and the activity of the protein can be determined. Preferably, the sequence of the mutated nucleotide is 80%, 90%, or 95% homologous with SEQ ID NO: 2.

A "non-essential" amino acid residue is a residue that can be altered from the wild-type sequence of PCSK6 without abolishing or, more preferably, without substantially altering its biological activity, whereas an "essential" amino acid residue results in such a change. For example, amino acid residues that are conserved among the polypeptides of the present invention are predicted to be particularly unamenable to alteration.

In some embodiments, the invention further involves making and using a substantially pure recombinant PCSK6 protein, or polypeptide fragment thereof. Recombinant PCSK6 is protein that is prepared using recombinant DNA technology, in which the gene expressing PCSK6 is expressed in a non-natural host, such as bacterial cells. For example, transformation or transfection can be used to introduce nucleic acid (e.g., DNA) encoding PCSK6 into a prokaryotic or eukaryotic host cell. Methods of preparing recombinant proteins are well-known to those skilled in the art. For example, recombinant PCSK6 (a) culturing a cell stably transformed with a gene comprising a nucleic acid molecule encoding the PCSK6 protein, wherein said nucleic acid comprises the nucleic acid sequence SEQ ID NO: 2; and (b) isolating and purifying the PCSK6 protein from the culture medium. As used herein, the terms PCSK6 "gene" and "recombinant gene" refer to nucleic acid molecules which include an open reading frame encoding a PCSK6 protein, such as a mammalian PCSK6 protein, and can further include non-coding regulatory sequences, and introns. These genes can be isolated from genomic DNA, cloned by recombinant means, or chemically synthesized.

Cardio-Renal Disease

Cardio-renal disease is a term that defines disorders of the heart and kidneys whereby "acute or chronic dysfunction in one organ may induce acute or chronic dysfunction of the other." See Ronco, C.; McCullough, S. D., European Heart Journal 31 (6): 703-711 (2010) and Zoccali et al., Kidney Int Suppl., (1):2-5 (2011). The heart and the kidneys are involved in maintaining hemodynamic stability and organ perfusion through an intricate network. These two organs communicate with one another through a variety of pathways in an interdependent relationship. The pathophysiology of cardio-renal disease can be attributed to two broad categories of "hemodynamic factors" such as low cardiac output, elevation of both intra-abdominal and central venous pressures, and non-hemodynamic factors or "cardiorenal connectors" such as neurohormonal and inflammatory activation. Braam et al., Nature Reviews Nephrology 10 (1): 48-55 (2013). In some embodiments, the cardio-renal disease involves a decrease in corin activity, which is involved in the processing of natriuretic peptides. The inventors have shown that corin is activated by PCSK6, and therefore can be used to treat cardio-renal disease. Renal failure is very common in patients suffering from congestive heart failure. Accordingly, in some embodiments of the invention, cardio-renal disease is a condition where treatment of congestive heart failure is limited by decline in kidney function.

In some embodiments, the cardio-renal disease being treated using PCSK6 or an effective fragment thereof is heart failure. Heart failure is a cardiovascular condition in which a problem with the structure or function of the heart impairs its ability to supply sufficient blood flow to meet the body's needs, characterized by compromised ventricular systolic or diastolic functions, or both. Heart failure may be manifested by symptoms of poor tissue perfusion alone (e.g., fatigue, poor exercise tolerance, or confusion) or by both symptoms of poor tissue perfusion and congestion of vascular beds (e.g., dyspnea, chest rates, pleural effusion, pulmonary edema, distended neck veins, congested liver, or peripheral edema). The most common causes of heart failure are coronary artery disease and high blood pressure. These problems can, in turn, result from decreased corin activity. In some embodiments, the type of heart failure being treated is congestive heart failure. Congestive heart failure represents a form of heart failure where cardiac output is low, in contrast with high output cardiac failure, in which the body's requirements for oxygen and nutrients are increased, and demand outstrips what the heart can provide. In further embodiments, the heart failure being treated is decompensated heart failure. Decompensated heart failure (DHF) is a worsening of the symptoms, typically shortness of breath (dyspnea), edema, and fatigue, in a patient with existing heart disease. DHF is a common and potentially serious cause of acute respiratory distress, which is caused by severe congestion of multiple organs by fluid that is inadequately circulated by the failing heart.

In other embodiments, the cardio-renal disease being treated by PCSK6 or an effective fragment thereof is hypertension. Hypertension is a chronic medical condition in which the blood pressure in the arteries is elevated in a persistent manner. A human subject is generally characterized as having hypertension if their blood pressure level is at or above 140/90 mmHg. Hypertension is classified as either primary hypertension or secondary hypertension; about 90-95% of cases being categorized as primary hypertension. Primary hypertension is high blood pressure with no obvious underlying medical cause. The remaining 5-10% of cases categorized as secondary hypertension are caused by other conditions that affect the kidneys, arteries, heart or endocrine system.

Measuring Decreased Corin Activity

Neurohormonal factors play an important role in cardio-renal disease. Corin is a serine protease that activates natriuretic peptides, which are neurohormonal factors, and is therefore an additional factor involved in cardio-renal disease. See U.S. application Ser. No. 10/926,083 and U.S. application Ser. No. 13/202,275, the disclosures of which are incorporated herein by reference, which describe the structure and activity of corin, and its use as a marker for heart failure. Corin-mediated natriuretic peptide production is essential for normal blood pressure and cardiac function, and likewise decreased corin activity has been shown to be involved in cardio-renal diseases such as hypertension and heart failure. Functional studies show that corin converts pro-atrial natriuretic peptide (ANP) and pro-brain natriuretic peptide (BNP) to active ANP and BNP (Yan et al., Proc. Natl. Acad. Sci., USA, 97(15):8525-8529 (2000)), which are cardiac hormones that regulate blood pressure and salt-water balance. Accordingly, in some embodiments, the cardio-renal disease involves decreased corin activity. For example, the corin activity can be decreased in an amount from 5% to 95% relative to the corin activity in a subject that does not have cardio-renal disease, and by amounts such as 10%, 20%, 30%, 40%, 50%, 60%, 70%, 80%, and 90%.

Decreased corin activity can be detected either by directly assaying the corin activity in a biological sample, or by determining the amount of corin present in the biological sample. Corin activity can be assayed, for example, by evaluating the ability of a sample to activate ANP and/or BNP, or by determining whether corin is activated or in its zymogen form. Decreased corin activity refers to corin activity that is lower than that seen in the general population, and can be identified through comparison of the corin activity of the subject with reference corin activity. Decreased corin activity can be used to determine which subjects are in need of treatment using PCSK6. Corin can be detected, directly or indirectly, using a variety of methods known in the art. For example, corin nucleic acid or portion thereof, corin protein or portion thereof, corin activity and combinations thereof can be detected using a variety of appropriate methods, including for example, methods for detecting the quantity of mRNA transcribed from the corin gene, the quantity of cDNA produced from the reverse transcription of the mRNA transcribed from the corin gene, the quantity of the corin polypeptide or protein encoded by the corn gene, or the activity of the corin polypeptide or protein encoded by the corin gene.

In assaying for a corin polypeptide or portion thereof, a variety of techniques are available in the art. They include but are not limited to radioimmunoassays, ELISA (Enzyme Linked Immunoradiometric Assays), "sandwich" immunoassays, immunoradiometric assays, in situ immunoassays (using e.g., colloidal gold, enzyme or radioisotope labels), western blot analysis, immunoprecipitation assays, immunofluorescent assays, PAGE-SDS and protein chips. One means to determine corin protein level involves (a) providing a biological sample containing corin polypeptide(s); and (b) measuring the amount of any immunospecific binding that occurs between an antibody reactive to the corin polypeptide or portion thereof and corin polypeptide(s) in the sample, in which the amount of immunospecific binding indicates the level of the corin polypeptide(s).

One of skill in the art will appreciate that any suitable biological sample obtained from an individual can be used to determine the level of corin activity. However, a preferred biological sample for assaying corin activity is plasma. Examples of suitable samples include biological fluids and tissue samples. Examples of a biological fluid that can be used in the methods include blood, plasma, urine and the like. Examples of a tissue sample include a tissue smear, a tissue scrape, and the like. Typically the sample is a biological fluid. In another embodiment, the sample comprises cardiomyocytes obtained from a subject's heart tissue.

Methods of Activating Corin

Another aspect of the invention provides a method of activating corin by contacting the corin with an effective amount of proprotein convertase subtilisin/kexin-6 (PCSK6) or an effective fragment thereof. As used herein the term contacting refers to bringing about direct contact between the PCSK6 and the corin protein of the subject such that they are in immediate proximity or association with each other so that PCSK6 is able to activate the corin protein. Contacting can occur, for example, as a result of administration of the PCSK6 such that it is delivered to tissue and/or biological fluids of the subject containing the corin protein.

Activating corin, as the phrase is used herein, refers to increasing the protease activity of corin. Since the corin protein is biochemically synthesized as a zymogen, it is activated by proteolytic cleavage, and experiments carried out by the inventors have shown that PCSK6 is capable of carrying out the proteolytic cleavage of the corin zymogen. An effective amount of PCSK6 is an amount capable of causing increased activity in corin. In some embodiments, the corin contacted by the PCSK6 is the inactive zymogen form of the corin protein.

The corin can be contacted in vivo, in vitro, or ex vivo. In vivo contact refers to contact within a living organism, such as a subject. In vitro contact refers to contact in a test tube, culture dish, or elsewhere outside a living organism. Ex vivo contact refers to PCSK6 contact with corin in or on tissue from an organism that has been placed in an external environment with the minimum alteration of natural conditions, such as tissue culture. The corin can be contacted in any tissue or biological fluid where corin may be present.

Corin is most abundant in the heart (e.g., cardiomyocytes), but is also expressed in blood vessels, uterine tissue, and renal tissue. For example, in some embodiments, the corin is activated in cardiomyocytes.

Administration and Formulation of PCSK6

Methods of the invention include administration of PCSK6 or an effective fragment thereof. A wide variety of different methods have been developed for formulation and administration of peptides (e.g., PCSK6). For example, peptides can be administered parenterally, orally, or by inhalation, transdermal, and intranasal routes. See Bak et al., AAPS J., 17(1):144-55 (2015). Preferred routes of administration include oral and parenteral administration. Parenteral administration includes PEGylation, hyperglycosylation, mannosylation, colloidal carriers including microparticles, nanoparticles, liposomes, carbon nanotubes, and micelles, and gel-based delivery. See Patel et al., Ther Deliv., 5(3):337-65 (2014). Oral administration includes methods such as ligand-protein conjugates, recombinant ligand-protein fusion proteins and ligand-modified carriers, lipid-based delivery systems, and nanoparticle formulations. See Pinto Reis et al., Ther Deliv., 4(2):251-65 (2013).

The data obtained from the cell culture assays and animal studies can be used in formulating a range of dosage for use in humans. The dosage may vary depending upon the dosage form employed and the route of administration. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from 0.001 to 30 mg/kg body weight, preferably 0.01 to 25 mg/kg body weight, more preferably 0.1 to 20 mg/kg body weight, and even more preferably 1 to 10 mg/kg, 2 to 9 mg/kg, 3 to 8 mg/kg, 4 to 7 mg/kg, or 5 to 6 mg/kg body weight. The protein or polypeptide can be administered one time per week for between 1 to 10 weeks, preferably between 2 to 8 weeks, more preferably between 3 to 7 weeks, and even more preferably for 4, 5, or 6 weeks. The skilled artisan will appreciate that certain factors may influence the dosage and timing required to effectively treat a mammal including, but not limited to, the severity of the disease or disorder, previous treatments, the general health and/or age of the mammal, and other diseases present. Moreover, treatment of a mammal with a therapeutically effective amount of a PCSK6 polypeptide or an effective fragment thereof can include a single treatment or, preferably, can include a series of treatments.

For intravenous, intramuscular, subcutaneous, or intraperitoneal administration, the PCSK6 may be combined with a sterile aqueous solution which is preferably isotonic with the blood of the recipient. Such formulations may be prepared by dissolving solid active ingredient in water containing physiologically compatible substances such as sodium chloride, glycine, and the like, and having a buffered pH compatible with physiological conditions to produce an aqueous solution, and rendering said solution sterile. The formulations may be present in unit or multi-dose containers such as sealed ampoules or vials.

Formulations suitable for parenteral administration conveniently comprise a sterile aqueous preparation of the active compound which is preferably made isotonic. Preparations for injections may also be formulated by suspending or emulsifying the compounds in non-aqueous solvent, such as vegetable oil, synthetic aliphatic acid glycerides, esters of higher aliphatic acids or propylene glycol.

The present invention is illustrated by the following example. It is to be understood that the particular examples, materials, amounts, and procedures are to be interpreted broadly in accordance with the scope and spirit of the invention as set forth herein.

EXAMPLE

Example 1: PCSK6-Mediated Corin Activation is Essential for Normal Blood Pressure To understand how corin is activated, corin wild-type (WT) and two inactive mutants: R801A, in which the activation site was abolished, and S985A, in which the catalytic serine was mutated (FIG. 2a), were expressed in HEK293 cells (FIG. 2b) and HL-1 cardiomyocytes (FIG. 2c), which are of human and mouse origins, respectively. On Western blots, corin zymogen migrated at ~170-200 kDa. An ~40-kDa band, representing the activated corin protease domain fragment (corin-p), was detected in WT. This band was present under reducing, but not nonreducing, conditions, because of a disulfide bond connecting the cleaved fragment to the propeptide (FIG. 2a). Consistently, the ~40-kDa band was absent in R801A mutant lacking the cleavage site. This band, however, appeared in the catalytically inactive mutant S985A, indicating that corin was activated specifically at Arg-801 by an unknown enzyme or enzymes in both HEK293 and HL-1 cells.

Different protease inhibitors were then tested for their effect on corin activation in transfected HEK293 cells. Western analysis showed that in the presence of benzamidine (serine protease inhibitor) and dec-RVKR-cmk (PCSK inhibitor), but not GM6001 (metalloproteinase inhibitor) and ALLM (cysteine protease inhibitor), corin activation was inhibited, as indicated by reduced levels of the ~40-kDa band and increased levels of an ~190-kDa zymogen band (FIG. 2d). The results suggested that a protease or proteases of the PCSK family might activate corin in these cells. Consistent with this hypothesis, the corin activation cleavage sequence is RMNKR↓, and PCSKs are known favoring double basic residues. Seidah et al., J Biol Chem 288, 21473-21481 (2013); Rockwell, et al., Chem Rev 102, 4525-4548 (2002).

The PCSK family has 9 members. PCSK1-9 plasmids were transfected in HEK293 cells expressing recombinant human corin. Western analysis showed that PCSK6 expression enhanced corin activation, as indicated by the loss of the corin zymogen band (FIG. 2e), suggesting that PCSK6 is a corin activator. By RT-PCR, PCSK6 mRNA was detected in HEK293 and HL-1 cells and in mouse and human hearts where corin is normally expressed. Yan et al., J Biol Chem 274, 14926-14935 (1999). The results were consistent with previous reports of PCSK6 expression in atrial and ventricular cardiomyocytes. Beaubien et al., Cell Tissue Res 279, 539-549 (1995). Using small interfering RNAs (siRNAs) targeting human PCSK6 and mouse Pcsk6 genes, the inventors showed that blocking PCSK6 expression inhibited corin activation cleavage in transfected HEK293 and HL-1 cells, whereas scrambled control siRNAs or siRNAs against PCSK1, 3 and 5 genes had no such effects under similar conditions (FIGS. 2f and g).

Figures 3A, 3B, 3C:
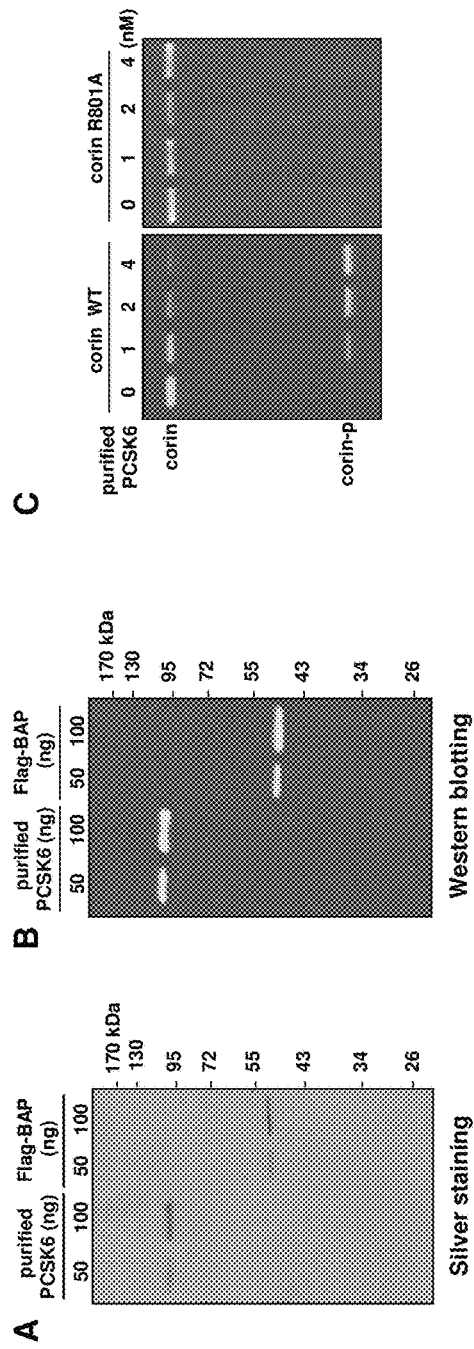
FIG. 3(a-c) provides graphs and images showing that purified recombinant human PCSK6 activated corin in a specific manner. (a) Recombinant human PCSK6, which contained a C-terminal flag tag, was expressed in HEK293 cells, purified from the conditioned medium, and analyzed by SDS-PAGE followed by silver staining (lanes 1 and 2). A flag-tagged bacterial alkaline phosphatase (BAP) was included as a control (lanes 3 and 4). (b) Purified PCSK6 was verified by Western analysis using an antibody against the flag tag. (c) Purified PCSK6 activated corin on the surface of HEK293 cells in a dose-depending manner. PCSK6-mediated corin activation was highly sequence-specific, as purified PCSK6 did not cleave corin mutant R801A lacking the cleavage site.

The inventors next expressed and purified recombinant human PCSK6, as shown in silver-stained gels and Western blots (FIGS. 3a and b). The inventor also showed that purified recombinant PCSK6 activated corin WT, but not R801A mutant, on HEK293 cells (FIG. 3c). These results show that purified recombinant human PCSK6 activated corin in a specific manner.

Figures 4A, 4B, 4C, 4D:
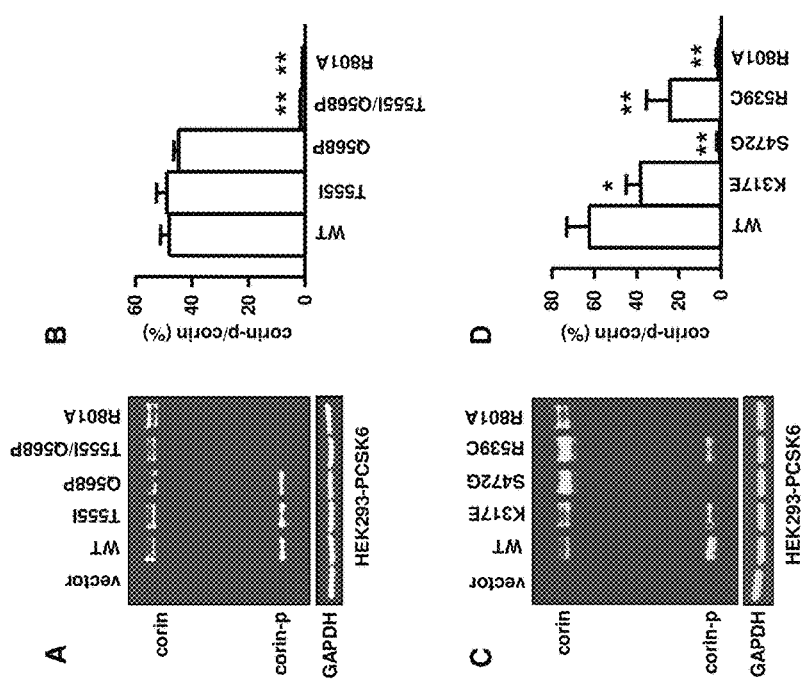
FIG. 4(a-d) provides graphs and images showing that PCSK6-mediated activation of naturally occurring CORIN mutants. (a) (b) Corin variant containing T555I/Q568P amino acid changes was identified in African Americans with hypertension and heart disease. In HEK293 cells, PCSK6-mediated corin activation was markedly reduced in corin T555I/Q568P mutant, but not in mutants with single mutation, either T555I or Q568P, as analyzed by Western blotting (a). Corin activation cleavage site mutant R801A was used as a control. The results were quantified by densitometry (b). **p<0.01 vs. WT. (c) (d) Naturally occurring mutations K317E, S472G and R539C were identified in patients with pre-eclampsia (K317E and S472G) and hypertension (R539C). In HEK293 cells, PCSK6-mediated corin activation was reduced by 39%, 99% and 62%, respectively, compared to that in WT corin, as analyzed by Western blotting (c). Corin activation cleavage site mutant R801A was used as a control. The results were quantified by densitometry (d). *p<0.05; **p<0.01 vs. WT.

In humans, CORIN gene variants and mutations have been identified in hypertensive patients. Cui et al., Nature 484, 246-250 (2012); Dong et al., J Biol Chem 288, 7867-7874 (2013). A CORIN variant allele causing T555I/Q568P amino acid changes was found in African Americans with hypertension and heart disease. Dries et al., Circulation 112, 2403-2410 (2005). Rame et al., Hypertension 49, 857-864 (2007). The variant protein encoded by this allele was shown to be defective in vitro and in vivo. Wang et al., Circ Res 103, 502-508 (2008). When both T555I/Q568P changes, but not single T555I or Q568P change, were present, corin activation was markedly reduced. The inventors tested PCSK6 on these variants. PCSK6-mediated activation cleavage was detected in corin WT and variants T555I or Q568P, but not variant T555I/Q568P (FIGS. 4a and b). In controls, no activation cleavage was detected in mutant R801A lacking the cleavage site.

Recently, corin was found to act in the pregnant uterus to promote spiral artery remodeling and prevent pregnancy-induced hypertension. Two CORIN mutations, K317E and S472G, were identified in pre-eclamptic patients. Cui et al., Nature 484, 246-250 (2012). Another CORIN mutation, R539C, also was found in a family with a history of hypertension. Dong et al., J Biol Chem 288, 17909-17916 (2013). In functional studies, K317E, S472G and R539C mutants all had markedly reduced pro-ANP processing activities. The inventors examined PCSK6-mediated activation in these mutants. By Western analysis, K317E, S472G and R539C mutants had 39%, 99% and 62% of reduction, respectively, in corin activation compared with WT corin (FIGS. 4c and d). Thus, naturally occurring CORIN mutations from patients with hypertension and pre-eclampsia were defective in PCSK6-mediated activation, which may explain the molecular basis underlying corin defects in these hypertensive patients.

Corin-mediated natriuretic peptide production is important for maintaining normal blood pressure and cardiac function. CORIN mutations reducing corin activity have been found in patients with hypertension. In patients with heart failure, high levels of unprocessed natriuretic peptides have been reported, indicating that corin activity is a rate-limiting factor in failing hearts. Dries et al., Circ Heart Fail 4, 107-110 (2011). In a mouse model of heart failure, corin overexpression was shown to improve cardiac function. Gladysheva et al., Hypertension 61, 327-332 (2013). PCSK6 has been reported to process growth factors and metalloproteinases. Constam et al., Genes Dev 14, 1146-1155 (2000). The inventors have shown that PCSK6 also acts as a primary corin activator and that PCSK6 represents a novel disease gene in hypertension. In humans, the PCSK6 gene was linked to high blood pressure in previous studies. Li et al., Chin Med J (Engl) 117, 382-388 (2004). Among PCSK family members, PCSK9 has been identified as a key regulator in LDL receptor recycling. Seidah et al., Circ Res 114, 1022-1036 (2014). PCSK9 inhibitors are being tested as cholesterol-lowering drugs. Thus, PCSK6 may be developed as a therapeutic agent to treat hypertension and heart disease.

Methods

Cell Culture.

HEK293 cells were cultured in DMEM with 10% fetal bovine serum (FBS). HL-1 cardiomyocytes were cultured in Claycomb medium with 10% FBS, and 4 mM L-glutamine. All cells were cultured at 37° C. in humidified incubators with 5% $CO_2$.

Plasmids.

Plasmids expressing human corin WT and mutants R801A, S985A, T555I, Q568P, T555I/Q568P, K317E, S472G and R539C were reported previously. Dong, N. et al., J Biol Chem 289, 17909-17916 (2014); Knappe et al., J Biol Chem 278, 52363-52370 (2003); Wu et al., J Biol Chem 277, 16900-16905. (2002). Plasmids expressing human PCSK1-9 were made by cloning respective cDNAs into pcNDA3.1 vector. Recombinant corin and PCSK proteins encoded by these plasmids contained a C-terminal V5 or flag tag for protein detection in Western blotting.

Transfection, Immunoprecipitaion, and Western Blotting.

HEK293 and HL-1 cells were transfected with corin or PCSK6 expression plasmids. After 48-72 h, cells were lysed in a buffer containing 25 mM Tris-HCl, pH 7.4, 150 mM NaCl, 1 mM EDTA, 1% (v/v) NP-40, and 1% (v/v) protease inhibitor cocktail. Recombinant corin and PCSK6 proteins were immunoprecipitated with an anti-V5 or anti-flag antibody. Western blotting was carried out to analyze corin expression and activation or PCSK6 expression with or without reducing agents. Percentage of corin activation (corin-p vs. corin fragments) was quantified by densitometric analysis of Western blots.

Cell Surface Protein Labeling.

HEK293 and HL-1 cells expressing recombinant corin in 6-well plates were incubated with 1.5 mL (200 µM) of membrane impermeable Sulfo-NHS-SS-biotin for 5 min. Qi et al., J Biol Chem 286, 20963-20969 (2011). A quenching solution was added to the wells and incubated on ice for 10 min. Cells were lysed in the lysis buffer. Labeled proteins were isolated with avidin-coupled agarose beads and analyzed by Western blotting.

Protease Inhibitors on Corin Activation Cleavage.

To identify the corin activator, corin activation cleavage was examined in HEK293 and HL-1 cells expressing corin in the presence of protease inhibitors including benzamidine (5 mM), GM6001 (50 µM), dec-RVKR-cmk (20 µM), or ALLM (N-acetyl-leucyl-leucyl-methionine 50 µM). Liao et al., J Biol Chem 282, 27728-27735 (2007). The inhibitors were added to the cells in separate wells. After 24 h, cell lysates were prepared and corin protein was analyzed by Western blotting.

PCSK6 Gene Knockdown.

On-TARGET plus SMARTpool siRNAs (5-100 nM) against human PCSK6 or mouse Pcsk6 genes were transfected into HEK293 or HL-1 cells expressing recombinant corin. Non-targeting scrambled siRNAs were used as negative controls. After 48-68 h at 37° C., corin expression on the cell surface and in cell lysate was analyzed by Western blotting. PCSK6 expression in siRNAs-treated cells was verified by Western blotting. Corin activation in the transfected cells was examined by Western analysis.

Expression and Purification of Recombinant PCSK6.

Stable HEK293 cells were established to produce human PCSK6 with a C-terminal flag tag. The cells were cultured in DMEM with 10% FBS and 600 µg/mL G418. At confluency, the cells were washed with PBS and cultured with Reduced-Serum Medium. After 72 h, the conditioned medium was collected, centrifuged (10 min at 17,000 g) to remove cell debris, and concentrated to ⅕ of the original volume using a Centrifugal filter unit at 4° C. The concentrated medium was incubated with anti-flag M2 affinity bead slurry in a volume ratio of 25:1 on a rotator at 4° C. for 2 h. After centrifugation, the beads were washed 5 times with a buffer (50 mM Tris-HCl, 150 mM NaCl, pH 7.4). PCSK6 protein was eluted in a solution with 160 ng/µL of flag peptide on a rotator at 4° C. for 1 h. After centrifugation, the supernatant containing purified PCSK6 was collected, and analyzed by SDS-PAGE followed by silver staining and Western blotting.

Corin Activation by Purified PCSK6.

Stable HEK293 cells expressing human corin were cultured in 6-well plates in DMEM with 10% FBS and 2 µM monensin. After confluency, the cells were washed and a mixture of reduced-serum medium and TBS solution in a ratio of 1:4 was added. Increasing concentrations of purified PCSK6 were added to the cell culture and incubated at 37° C. After 2 h, cell surface proteins were labeled and corin protein was analyzed by Western blotting.

Statistical Analysis.

Data are presented as means±S.D. Statistical analysis was done using the GraphPad Prism software. Comparisons for three or more groups were made using one-way ANOVA followed by Tukey's post test or two-way ANOVA followed by Bonferroni post test, as specified in figure legends for each study. A p value of <0.05 was considered as statistically significant.

The complete disclosure of all patents, patent applications, and publications, and electronically available materials cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method of treating a cardio-renal disease, comprising administering to a subject in need thereof an amount of proprotein convertase subtilisin/kexin-6 (PCSK6) effective to activate native corin in the subject.

2. The method of claim 1, wherein the cardio-renal disease involves decreased corin activity.

3. The method of claim 1, wherein the cardio-renal disease is heart failure.

4. The method of claim 3, wherein the heart failure is congestive heart failure.

5. The method of claim 1, wherein the cardio-renal disease is decompensated heart failure.

6. The method of claim 1, wherein the cardio-renal disease is hypertension.

7. The method of claim 1, wherein the proprotein convertase subtilisin/kexin-6 is recombinant PCSK6.

8. The method of claim 1, wherein the proprotein convertase subtilisin/kexin-6 is administered in a pharmaceutically acceptable carrier.

9. The method of claim 1, wherein an assay of a biological sample from the subject shows the subject exhibits decreased corin activity.

10. The method of claim 9, wherein the assay is an immunoassay.

11. The method of claim 1, wherein the subject is human.

12. The method of claim 1, wherein the PCSK6 recognizes native corin in the subject.

13. A method of treating decompensated heart failure, comprising administering to a subject in need thereof an amount of proprotein convertase subtilisin/kexin-6 (PCSK6) effective to activate native corin in the subject.

14. The method of claim 1, the amount of PCSK6 effective to activate native corin in the subject comprising 0.1 to 20 mg/kg body weight of the subject.

* * * * *

SEQUENCE LISTING

<160> NUMBER OF SEQ ID NOS: 2

<210> SEQ ID NO 1
<211> LENGTH: 969
<212> TYPE: PRT
<213> ORGANISM: Homo sapiens

<400> SEQUENCE: 1

Met Pro Pro Arg Ala Pro Pro Ala Pro Gly Pro Arg Pro Pro Pro Arg
1               5                   10                  15

Ala Ala Ala Ala Thr Asp Thr Ala Ala Gly Ala Gly Gly Ala Gly Gly

-continued

```
                20                  25                  30
Ala Gly Gly Ala Gly Gly Pro Gly Phe Arg Pro Leu Ala Pro Arg Pro
                35                  40                  45
Trp Arg Trp Leu Leu Leu Leu Ala Leu Pro Ala Ala Cys Ser Ala Pro
        50                  55                  60
Pro Pro Arg Pro Val Tyr Thr Asn His Trp Ala Val Gln Val Leu Gly
65                  70                  75                  80
Gly Pro Ala Glu Ala Asp Arg Val Ala Ala His Gly Tyr Leu Asn
                85                  90                  95
Leu Gly Gln Ile Gly Asn Leu Glu Asp Tyr Tyr His Phe Tyr His Ser
                100                 105                 110
Lys Thr Phe Lys Arg Ser Thr Leu Ser Ser Arg Gly Pro His Thr Phe
            115                 120                 125
Leu Arg Met Asp Pro Gln Val Lys Trp Leu Gln Gln Glu Val Lys
                130                 135                 140
Arg Arg Val Lys Arg Gln Val Arg Ser Asp Pro Gln Ala Leu Tyr Phe
145                 150                 155                 160
Asn Asp Pro Ile Trp Ser Asn Met Trp Tyr Leu His Cys Gly Asp Lys
                165                 170                 175
Asn Ser Arg Cys Arg Ser Glu Met Asn Val Gln Ala Ala Trp Lys Arg
            180                 185                 190
Gly Tyr Thr Gly Lys Asn Val Val Val Thr Ile Leu Asp Asp Gly Ile
            195                 200                 205
Glu Arg Asn His Pro Asp Leu Ala Pro Asn Tyr Asp Ser Tyr Ala Ser
        210                 215                 220
Tyr Asp Val Asn Gly Asn Asp Tyr Asp Pro Ser Pro Arg Tyr Asp Ala
225                 230                 235                 240
Ser Asn Glu Asn Lys His Gly Thr Arg Cys Ala Gly Glu Val Ala Ala
                245                 250                 255
Ser Ala Asn Asn Ser Tyr Cys Ile Val Gly Ile Ala Tyr Asn Ala Lys
            260                 265                 270
Ile Gly Gly Ile Arg Met Leu Asp Gly Asp Val Thr Asp Val Val Glu
            275                 280                 285
Ala Lys Ser Leu Gly Ile Arg Pro Asn Tyr Ile Asp Ile Tyr Ser Ala
        290                 295                 300
Ser Trp Gly Pro Asp Asp Asp Gly Lys Thr Val Asp Gly Pro Gly Arg
305                 310                 315                 320
Leu Ala Lys Gln Ala Phe Glu Tyr Gly Ile Lys Lys Gly Arg Gln Gly
                325                 330                 335
Leu Gly Ser Ile Phe Val Trp Ala Ser Gly Asn Gly Gly Arg Glu Gly
            340                 345                 350
Asp Tyr Cys Ser Cys Asp Gly Tyr Thr Asn Ser Ile Tyr Thr Ile Ser
            355                 360                 365
Val Ser Ser Ala Thr Glu Asn Gly Tyr Lys Pro Trp Tyr Leu Glu Glu
        370                 375                 380
Cys Ala Ser Thr Leu Ala Thr Thr Tyr Ser Ser Gly Ala Phe Tyr Glu
385                 390                 395                 400
Arg Lys Ile Val Thr Thr Asp Leu Arg Gln Arg Cys Thr Asp Gly His
                405                 410                 415
Thr Gly Thr Ser Val Ser Ala Pro Met Val Ala Gly Ile Ile Ala Leu
            420                 425                 430
Ala Leu Glu Ala Asn Ser Gln Leu Thr Trp Arg Asp Val Gln His Leu
        435                 440                 445
```

```
Leu Val Lys Thr Ser Arg Pro Ala His Leu Lys Ala Ser Asp Trp Lys
    450                 455                 460

Val Asn Gly Ala Gly His Lys Val Ser His Phe Tyr Gly Phe Gly Leu
465                 470                 475                 480

Val Asp Ala Glu Ala Leu Val Val Glu Ala Lys Lys Trp Thr Ala Val
                485                 490                 495

Pro Ser Gln His Met Cys Val Ala Ala Ser Asp Lys Arg Pro Arg Ser
                500                 505                 510

Ile Pro Leu Val Gln Val Leu Arg Thr Thr Ala Leu Thr Ser Ala Cys
                515                 520                 525

Ala Glu His Ser Asp Gln Arg Val Val Tyr Leu Glu His Val Val Val
                530                 535                 540

Arg Thr Ser Ile Ser His Pro Arg Arg Gly Asp Leu Gln Ile Tyr Leu
545                 550                 555                 560

Val Ser Pro Ser Gly Thr Lys Ser Gln Leu Leu Ala Lys Arg Leu Leu
                565                 570                 575

Asp Leu Ser Asn Glu Gly Phe Thr Asn Trp Glu Phe Met Thr Val His
                580                 585                 590

Cys Trp Gly Glu Lys Ala Glu Gly Gln Trp Thr Leu Glu Ile Gln Asp
        595                 600                 605

Leu Pro Ser Gln Val Arg Asn Pro Glu Lys Gln Gly Lys Leu Lys Glu
        610                 615                 620

Trp Ser Leu Ile Leu Tyr Gly Thr Ala Glu His Pro Tyr His Thr Phe
625                 630                 635                 640

Ser Ala His Gln Ser Arg Ser Arg Met Leu Glu Leu Ser Ala Pro Glu
                645                 650                 655

Leu Glu Pro Pro Lys Ala Ala Leu Ser Pro Ser Gln Val Glu Val Pro
                660                 665                 670

Glu Asp Glu Glu Asp Tyr Thr Ala Gln Ser Thr Pro Gly Ser Ala Asn
                675                 680                 685

Ile Leu Gln Thr Ser Val Cys His Pro Glu Cys Gly Asp Lys Gly Cys
        690                 695                 700

Asp Gly Pro Asn Ala Asp Gln Cys Leu Asn Cys Val His Phe Ser Leu
705                 710                 715                 720

Gly Ser Val Lys Thr Ser Arg Lys Cys Val Ser Val Cys Pro Leu Gly
                725                 730                 735

Tyr Phe Gly Asp Thr Ala Ala Arg Arg Cys Arg Arg Cys His Lys Gly
                740                 745                 750

Cys Glu Thr Cys Ser Ser Arg Ala Ala Thr Gln Cys Leu Ser Cys Arg
        755                 760                 765

Arg Gly Phe Tyr His His Gln Glu Met Asn Thr Cys Val Thr Leu Cys
        770                 775                 780

Pro Ala Gly Phe Tyr Ala Asp Glu Ser Gln Lys Asn Cys Leu Lys Cys
785                 790                 795                 800

His Pro Ser Cys Lys Lys Cys Val Asp Glu Pro Glu Lys Cys Thr Val
                805                 810                 815

Cys Lys Glu Gly Phe Ser Leu Ala Arg Gly Ser Cys Ile Pro Asp Cys
        820                 825                 830

Glu Pro Gly Thr Tyr Phe Asp Ser Glu Leu Ile Arg Cys Gly Glu Cys
        835                 840                 845

His His Thr Cys Gly Thr Cys Val Gly Pro Gly Arg Glu Glu Cys Ile
850                 855                 860
```

| | | | | | | | | | | | | | |
|---|---|---|---|---|---|---|---|---|---|---|---|---|---|
|His|Cys|Ala|Lys|Asn|Phe|His|Phe|His|Asp|Trp|Lys|Cys|Val|Pro|Ala|
|865| | | | |870| | | |875| | | | |880|

| | | | | | | | | | | | | |
|---|---|---|---|---|---|---|---|---|---|---|---|---|
|Cys|Gly|Glu|Gly|Phe|Tyr|Pro|Glu|Glu|Met|Pro|Gly|Leu|Pro|His|Lys|
| | | | |885| | | | |890| | | | |895|

| | | | | | | | | | | | | |
|---|---|---|---|---|---|---|---|---|---|---|---|---|
|Val|Cys|Arg|Arg|Cys|Asp|Glu|Asn|Cys|Leu|Ser|Cys|Ala|Gly|Ser|Ser|
| | | |900| | | | |905| | | | |910| |

| | | | | | | | | | | | | |
|---|---|---|---|---|---|---|---|---|---|---|---|---|
|Arg|Asn|Cys|Ser|Arg|Cys|Lys|Thr|Gly|Phe|Thr|Gln|Leu|Gly|Thr|Ser|
| | |915| | | |920| | | |925| | | | |

| | | | | | | | | | | | | |
|---|---|---|---|---|---|---|---|---|---|---|---|---|
|Cys|Ile|Thr|Asn|His|Thr|Cys|Ser|Asn|Ala|Asp|Glu|Thr|Phe|Cys|Glu|
| |930| | | |935| | | |940| | | | | |

| | | | | | | | | | | | | |
|---|---|---|---|---|---|---|---|---|---|---|---|---|
|Met|Val|Lys|Ser|Asn|Arg|Leu|Cys|Glu|Arg|Lys|Leu|Phe|Ile|Gln|Phe|
|945| | | |950| | | |955| | | | |960| |

| | | | | | |
|---|---|---|---|---|---|
|Cys|Cys|Arg|Thr|Cys|Leu|Leu|Ala|Gly|
| | | |965| | | | | |

<210> SEQ ID NO 2
<211> LENGTH: 4570
<212> TYPE: DNA
<213> ORGANISM: Homo sapiens

<400> SEQUENCE: 2

```
tcgcgggccg aggacgcctc tggggcggca ccgcgtcccg agagcccag aagtcggcgg      60
ggaagttccc ccggtggggg gcgtttcggg cctcccggac ggctctcggc cccgagccc    120
ggtcgcagga gcgcgggccc gggggcggga acgccgcgcg gccgcctcct cctccccggc   180
tcccgcccgc ggcggtgttg gcggcggcgg tggcggcggc ggcggcgctt ccccggcgcg   240
gagcggcttt aaaaggcggc actccacccc ccggcgcact cgcagctcgg gcgccgcgcg   300
agcctgtcgc cgctatgcct ccgcgcgcgc cgcctgcgcc cgggcccgg ccgccgcccc    360
gggccgccgc cgccaccgac accgccgcgg gcgcggggggg cgcgggggggc gcgggggggcg  420
ccggcgggcc cgggttccgg ccgctcgcgc gcgtccctg gcgctggctg ctgctgctgg    480
cgctgcctgc cgcctgctcc gcgccccgc cgcgccccgt ctacaccaac cactgggcgg    540
tgcaagtgct gggcggcccg gccgaggcgg accgcgtggc ggcggcgcac gggtacctca   600
acttgggcca gattggaaac ctggaagatt actaccattt ttatcacagc aaaaccttta   660
aaagatcaac cttgagtagc agaggccctc acaccttcct cagaatggac ccccaggtga   720
aatggctcca gcaacaggaa gtgaaacgaa gggtgaagag acaggtgcga agtgacccgc   780
aggcccttta cttcaacgac cccatttggt ccaacatgtg gtacctgcat gtggcgaca    840
agaacagtcg ctgccggtcg gaaatgaatg tccaggcagc gtggaagagg ggctacacag   900
gaaaaaacgt ggtggtcacc atccttgatg atggcataga gagaaatcac cctgacctgg   960
ccccaaatta tgattcctac gccagctacg acgtgaacgg caatgattat gacccatctc  1020
cacgatatga tgccagcaat gaaaataaac acggcactcg ttgtgcggga gaagttgctg  1080
cttcagcaaa caattcctac tgcatcgtgg catagcgta caatgccaaa ataggaggca   1140
tccgcatgct ggacggcgat gtcacagatg tggtcgaggc aaagtcgctg ggcatcagac  1200
ccaactacat cgacatttac agtgccagct gggggccgga cgacgacggc aagacggtgg  1260
acgggcccgg ccgactggct aagcaggctt tcgagtatgg cattaaaaag ggccggcagg  1320
gcctgggctc cattttcgtc tgggcatctg gaatggcgg gagagagggg gactactgct  1380
cgtgcgatgg ctacaccaac agcatctaca ccatctccgt cagcagcgcc accgagaatg  1440
gctacaagcc ctggtacctg gaagagtgtg cctccaccct ggccaccacc tacagcagtg  1500
```

```
gggccttttta tgagcgaaaa atcgtcacca cggatctgcg tcagcgctgt accgatggcc    1560
acactgggac ctcagtctct gcccccatgg tggcgggcat catcgccttg gctctagaag    1620
caaacagcca gttaacctgg agggacgtcc agcacctgct agtgaagaca tcccggccgg    1680
cccacctgaa agcgagcgac tggaaagtga acggcgcggg tcataaagtt agccatttct    1740
atggatttgg tttggtggac gcagaagctc tcgttgtgga ggcaaagaag tggacagcag    1800
tgccatcgca gcacatgtgt gtggccgcct cggacaagag acccaggagc atccccttag    1860
tgcaggtgct gcggactacg gccctgacca gcgcctgcgc ggagcactcg gaccagcggg    1920
tggtctactt ggagcacgtg gtggttcgca cctccatctc acacccacgc cgaggagacc    1980
tccagatcta cctggtttct ccctcgggaa ccaagtctca acttctggca aagaggttgc    2040
tggatctttc caatgaaggg tttacaaact gggaattcat gactgtccac tgctggggag    2100
aaaaggctga agggcagtgg accttggaaa tccaagatct gccatcccag gtccgcaacc    2160
cggagaagca agggaagttg aaagaatgga gcctcatact gtatggcaca gcagagcacc    2220
cgtaccacac cttcagtgcc catcagtccc gctcgcggat gctggagctc tcagcccag    2280 agctggagcc acccaaggct gccctgtcac cctcccaggt ggaagttcct gaagatgagg    2340
aagattacac agctcaatcc accccaggct ctgctaatat tttacagacc agtgtgtgcc    2400
atccggagtg tggtgacaaa ggctgtgatg gccccaatgc agaccagtgc ttgaactgcg    2460
tccacttcag cctggggagt gtcaagacca gcaggaagtg cgtgagtgtg tgccccttgg    2520
gctactttgg ggacacagca gcaagacgct gtcgccggtg ccacaagggg tgtgagacct    2580
gctccagcag agctgcgacg cagtgcctgt cttgccgccg cgggttctat caccaccagg    2640
agatgaacac ctgtgtgacc ctctgtcctg caggatttta tgctgatgaa agtcagaaaa    2700
attgccttaa atgccacccca agctgtaaaa agtgcgtgga tgaacctgag aaatgtactg    2760
tctgtaaaga aggattcagc cttgcacggg gcagctgcat tcctgactgt gagccaggca    2820
cctactttga ctcagagctg atcagatgtg gggaatgcca tcacacctgc ggaacctgcg    2880
tggggccagg cagagaagag tgcattcact gtgcgaaaaa cttccacttc cacgactgga    2940
agtgtgtgcc agcctgtggt gagggcttct acccagaaga gatgccgggc ttgccccaca    3000
aagtgtgtcg aaggtgtgac gagaactgct tgagctgtgc aggctccagc aggaactgta    3060
gcaggtgtaa gacgggcttc acacagctgg ggacctcctg catcaccaac cacacgtgca    3120
gcaacgctga cgagacattc tgcgagatgg tgaagtccaa ccggctgtgc gaacggaagc    3180
tcttcattca gttctgctgc cgcacgtgcc tcctggccgg gtaagggtgc ctagctgccc    3240
acagagggca ggcactccca tccatccatc cgtccacctt cctccagact gtcggccaga    3300
gtctgtttca ggagcggcgc cctgcacctg acagctttat ctccccagga gcagcatctc    3360
tgagcaccca agccaggtgg gtggtggctc ttaaggaggt gttcctaaaa tggtgatatc    3420
ctctcaaatg ctgcttgttg gctccagtct tccgacaaac taacaggaac aaaatgaatt    3480
ctgggaatcc acagctctgg cttttggagca gcttctggga ccataagttt actgaatctt    3540
caagaccaaa gcagaaaaga aaggcgcttg gcatcacaca tcactcttct ccccgtgctt    3600
ttctgcggct gtgtagtaaa tctccccggc ccagctggcg aaccctgggc catcctcaca    3660
tgtgacaaag ggccagcagt ctacctgctc gttgcctgcc actgagcagt ctggggacgg    3720
tttggtcaga ctataaataa gataggtttg agggcataaa atgtatgacc actggggccg    3780
gagtatctat ttctacatag tcagctactt ctgaaactgc agcagtggct tagaaagtcc    3840
aattccaaag ccagaccaga agattctatc ccccgcagcg ctctcctttg agcaagccga    3900
```

```
gctctccttg ttaccgtgtt ctgtctgtgt cttcaggagt ctcatggcct gaacgaccac    3960
ctcgacctga tgcagagcct tctgaggaga ggcaacagga ggcattctgt ggccagccaa    4020
aaggtacccc gatggccaag caattcctct gaacaaaatg taaagccagc catgcattgt    4080
taatcatcca tcacttccca ttttatggaa ttgcttttaa aatacatttg gcctctgccc    4140
ttcagaagac tcgtttttaa ggtggaaact cctgtgtctg tgtatattac aagcctacat    4200
gacacagttg gatttattct gccaaacctg tgtaggcatt ttataagcta catgttctaa    4260
tttttaccga tgttaattat tttgacaaat atttcatata ttttcattga aatgcacaga    4320
tctgcttgat caattcsctt gaatagggaa gtaacatttg ccttaaattt tttcgacctc    4380
gtctttctcc atattgtcct gctcccctgt ttgacgacag tgcatttgcc ttgtcacctg    4440
tgagctggag agaacccaga tgttgtttat tgaatctaca actctgaaag agaaatcaat    4500
gaagcaagta caatgttaac cctaaattaa taaaagagtt aacatcccat ggcaaaaaaa    4560
aaaaaaaaaa                                                          4570
```